United States Patent [19]

Boiarski et al.

[11] 4,268,460
[45] May 19, 1981

[54] NEBULIZER

[75] Inventors: Anthony A. Boiarski, Columbus; Ross G. Luce, Westerville, both of Ohio

[73] Assignee: Warner-Lambert Company, Morris Plains, N.J.

[21] Appl. No.: 127,350

[22] Filed: Mar. 5, 1980

Related U.S. Application Data

[63] Continuation of Ser. No. 860,006, Dec. 12, 1977, abandoned.

[51] Int. Cl.³ .......................................... A61M 11/02
[52] U.S. Cl. .................................. 261/1; 128/200.16; 128/200.21; 239/338; 261/DIG. 65; 261/DIG. 48; 261/78 A
[58] Field of Search ............... 261/1, 78 A, DIG. 48, 261/DIG. 65; 128/200.16, 200.21; 239/338

[56] References Cited

U.S. PATENT DOCUMENTS

| | | | |
|---|---|---|---|
| 2,532,554 | 12/1950 | Joeck | 261/DIG. 48 |
| 2,831,666 | 4/1958 | Compton | 261/DIG. 48 |
| 3,278,165 | 10/1966 | Gaffney | 261/DIG. 48 |
| 3,326,467 | 6/1967 | Fortman | 261/DIG. 48 |
| 3,545,947 | 12/1970 | Gray et al. | 261/1 |
| 3,603,308 | 9/1971 | Spradling et al. | 128/200.21 |
| 4,087,495 | 5/1978 | Umehara | 261/1 |
| 4,198,969 | 4/1980 | Virag | 128/200.21 |

*Primary Examiner*—Frank W. Lutter
*Assistant Examiner*—Gregory N. Clements
*Attorney, Agent, or Firm*—Louis S. Gillow

[57] ABSTRACT

A nebulizer for use in connection with a lung ventilating system characterized in providing a dual stage atomization of medicament carrying liquid. A first stage develops an aerosol exhibiting an initial, relatively larger average liquid particle size which is introduced to a chamber at a given stagnation pressure. From that chamber, a second atomization is carried out by passing the gas entrained liquid particles through a knife edge orifice to produce a rapid expansion free-jet flow and consequent particle breakdown to achieve a desired particle size distribution.

10 Claims, 9 Drawing Figures

NEBULIZER

This is a continuation of application Ser. No. 860,006, filed Dec. 12, 1977, now abandoned.

BACKGROUND

Intermittent, positive pressure breathing systems represent an important facet in medical respiratory therapy. In general, these systems respond to inspiratory impulses to deliver quantities of oxygen and/or other supportive gases to a patient under a mild positive pressure. Gas flow communication between the patient and the system is by a mask or mouthpiece coupled through tubing to a somewhat elaborate control apparatus serving to regulate gas flow, pressure and the like. Among the advantages of its use, the therapy has been described as serving to increase tidal volume and total minute ventilation; to decrease the work or "cost" of breathing, to facilitate the elimination of carbon dioxide by increasing alveolar ventilation; to increase arterial and tissue oxygen tension; to provide mechanical bronchodilation, and to prevent or correct atelectasis.

To further expand the therapeutic capability of the systems, the common practice has been to generate medicament carrying aerosols within the treatment mechanism conducting oxygen to the patient. Thus incorporated, the system retains an advantageous capability of delivering all medications used in aerosol therapy, i.e. bronchodilators, mucolytics, detergents, antibiotics, proteolytics, anti-foaming agents and wetting agents. For optimum performance in carrying out aerosol therapy it has been determined that the particle or droplet size distribution of the aerosol mist should be optimized to achieve requisite introduction of medicament into the lung. For example the lung is structured having twenty-three generations of subdivisions, the trachea being the zeroeth generation, the left and right main branches forming the first generation, etc. Should the size of the medicament carrying aerosol particles be too large, it is opined that they would be impacted upon the oral pharynx and not reach the bronchial tract, thus rendering the therapy substantially ineffective. On the other hand, some authority suggests that where the aerosol particles are too fine, i.e. of too small an average diameter, significant portions of the mist may not be absorbed but will be exhaled. Accordingly, a most desired medicament carrying aerosol development is one wherein an optimized distribution of droplet or particle size is achieved. For example, it is desirable that the particle size distribution be somewhat monodisperse, the greater number of particles having a diameter of about 2 microns. Particles of that diametric extent would be suited for a deposition throughout a sufficient number of generations of the lung extending toward the alveoli.

Considerations of efficient clinical practice require that the nebulizer devices which generate the medicament carrying aerosols or "micro mists" be fabricable at cost levels such that both the nebulizer and connecting flexible tubing, mouthpieces and the like leading from more complex control equipment to the patient be disposable after one use. This feature of disposability permits a clinical assurance of establishing requisite sterility for all components and as a consequence, minimal opportunity for human error to occur.

Nebulizer devices currently used or proposed generally fail to meet all of the above-discussed criteria. For instance, disposable devices typically in clinical use form the aerosol mist by introducing a stream of medicament carrying liquid into the gas stream leading to the mouthpiece or mask. Sometimes identified as the "Bernoulli Effect", a jet of gas interacts with the liquid stream to shear off droplets. Conventionally some form of spherical target is positioned downstream from the point of liquid introduction to achieve a break up of the larger of these air entrained droplets. Generally, these devices evolve a particulate distribution of the aerosol having a relatively large number of particles of larger diameter and mass. These larger particles have only marginal therapeutic effect upon reaching the lung. Ultrasonic devices have been proposed but are regarded as too expensive to manufacture for requisite disposability and, additionally, for typical application, these devices tend to produce too dense a cloud of aerosol for practical utilization within the tubular conduits typically provided, in conjunction with lung ventilating equipment.

SUMMARY

The present invention is addressed to a system, method and apparatus having a capability for generating micro-mists exhibiting liquid particle size distribution optimized for aerosol therapy, while remaining fabricable at costs permitting diposal of the apparatus following a single clinical usage. Characterized in providing dual stage atomization of medicament carrying liquid, the inventive approach first develops an aerosol constituted as having an initial, relatively larger average liquid particle size. These initial, air entrained particles then are introduced to a second atomization stage wherein they are subjected to secondary breakup by aerodynamic forces produced in a rapid expansion sonic orifice-free-jet flow. By select control over certain of the parameters of the system, for example initial particle or droplet size and/or free-jet orifice diameter, a particle size distribution closely conforming to the precise desires of the operator for individual therapeutic treatment can be developed.

Another feature and object of the invention is to provide a nebulizer apparatus which is connectable with a source of life-supporting gas typically available in a hospital environment. The apparatus incorporates a first atomization stage which is configured to simultaneously communicate with the source of gas and a source of liquid to form a first particulate dispersion of the liquid which is entrained within the gas. These liquid particles may be considered as exhibiting an average particle diameter, $D_I$, and a surface tension, $S$, while the gas may be considered to exhibit a density, $\rho_g$. The apparatus further includes a second atomizer stage communicating with the first stage and having an input zone which receives the gas-entrained first particulate dispersion at a stagnation pressure, $P_o$. The second stage further incorporates an exit orifice having a diameter, $d_o$, through which the dispersion is expelled, the gas being at supersonic velocities. With the arrangement, the gas and entrained liquid droplets move under flow conditions according to the expression:

$$\rho_g u_r^2 \geq W_e(S/D_I),$$

where
$u_r$ is the relative velocity between a given liquid particle and the velocity of the gas and $W_e$ is a Weber number of value effective to carry out a stripping mechanism breakdown of the liquid particles. This Weber number value is equal to or greater than a critical Weber number value. Additionally, it is preferred that the exit orifice diameter, $d_o$, be selected to derive a liquid particle conversion efficiency, $\epsilon$, of at least about 50 percent.

Another object of the invention is to provide a method for generating an aerosol of selected particle size distribution from a liquid source. This method includes the step of initially atomizing the liquid in the presence of a gas flow to produce a first particulate dispersion of the liquid entrained within the gas. Next, the particulate dispersion, under a given stagnation pressure, is expelled through an orifice to effect a free-jet transference and impart supersonic velocities to the gas to form a second particulate dispersion of particles having a smaller average diameter. According to the method, the liquid particles within the first dispersion exhibit a characteristic particle oscillation period, $\tau$, and remain under the size-breakdown influence of the gas supersonic velocities subsequent to the free-jet transference for an action time interval, $t_a$, equal to or greater than that oscillation period.

A further object of the invention is to provide a lung ventilating system of a variety wherein life-supporting gas is conveyed under a positive pressure through conduit means from a pressurized source into the lung of a patient. The invention provides for the introduction of nebulized liquid into the conduit using apparatus which includes first and second atomizer stages arranged in serial fashion, the second stage providing for a free-jet acceleration transference of a first suspension of particles through an orifice leading to the conduit, the transference effecting formation of a fine particulate suspension.

Other objects of the invention will, in part, be obvious and will, in part, appear hereinafter.

The invention, accordingly, comprises the system, apparatus and method possessing the construction, combination of elements, arrangements of parts and steps which are exemplified by the following detailed disclosure.

For a fuller understanding of the nature and objects of the invention, reference should be had to the following detailed description taken in connection with the accompanying drawings.

BRIEF DESCRIPTION OF THE DRAWINGS

FIG. 1 is a schematic and pictorial representation of a lung ventilating system including the nebulizer innovation of the instant invention;

FIG. 2 is a schematic representation of liquid particle breakup, showing stripping as well as deformation breakup mechanisms;

DETAILED DESCRIPTION

Figures 1, 2:
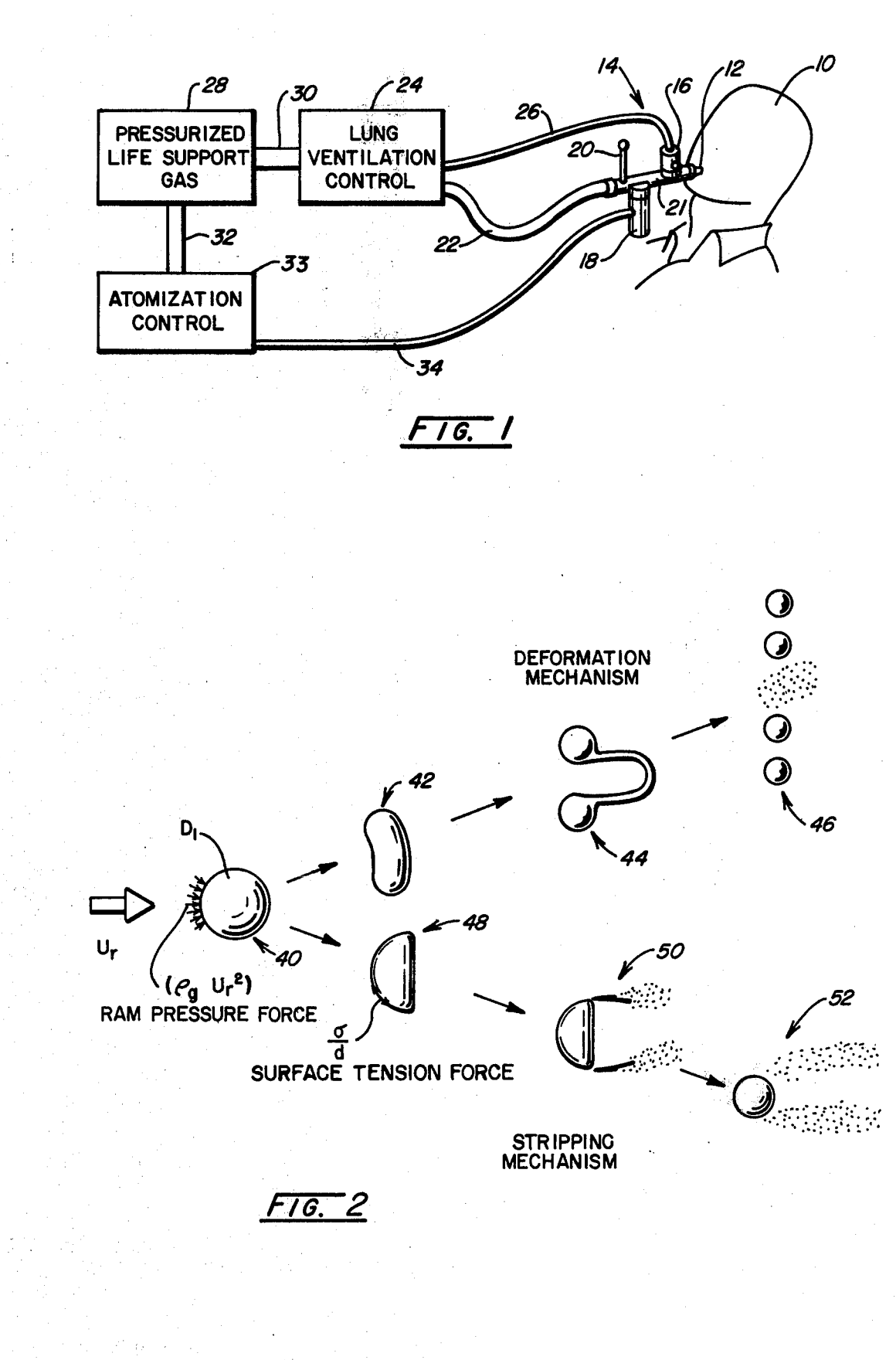
Figure 3:
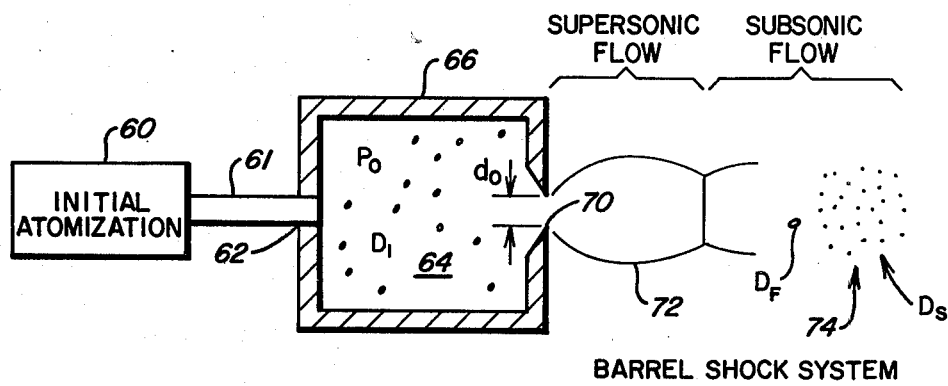
FIG. 3 is a schematic representation of a free-jet atomization arrangement for evolving a stripping mechanism liquid droplet breakup.
Figure 9:
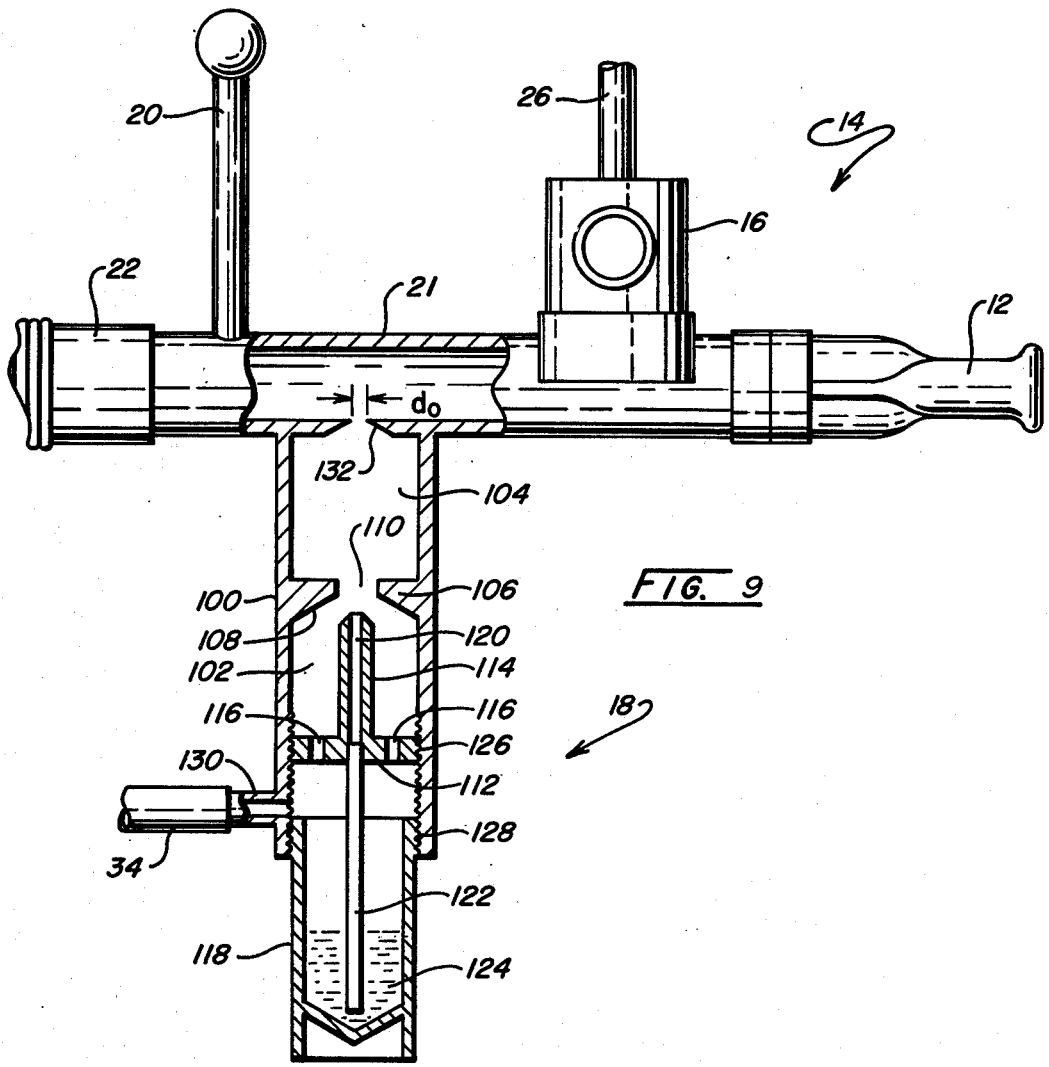
FIG. 9 is an embodiment of a nebulizer arrangement according to the invention with portions cut away to reveal internal structure.

As used herein, atomization refers to the process of creating an aerosol of minute droplets. The nebulizer approach of the present invention involves a secondary breakup in the initially atomized droplets of a medicament carrying liquid using a supersonic free-jet expansion through a relatively small orifice. The system of the invention utilizes the basic controls currently in use in conjunction with current disposable nebulizer devices deriving atomization through the "Bernoulli Effect" discussed above. Referring to FIG. 1, a schematic illustration of the disposable components of a lung ventilation system according to the invention are revealed in conjunction with representations of conventional life support gas supplies and lung ventilation control equipment. In the figure, a patient is shown at 10 receiving aerosol therapy. With this arrangement, the patient orally retains the mouthpiece 12 of a disposable, positive-negative unit 14 or apparatus for the controlled reception of oxygen and other optionally provided support of gases. Unit 14 is configured incorporating an exhaust valve 16 and a nebulizer device according to the invention at 18. An upwardly protruding stem 20 terminating in a ball joint component is provided to secure the device 14 to an overhead support (not shown) to aid the patient in retaining mouthpiece 12 in proper position. Support gas at low positive pressure is introduced into device 14 through flexible discardable tubing 22 from a lung ventilation control apparatus represented schematically by block 24. The control provided at block 24 serves to respond to patient breathing activity to inflate the lung until a preset pressure has been reached, at which time the inspiratory phase is halted and expiration commences. Generally, such devices also can operate in predetermined automatically timed control fashion as opposed to a patient respiratory demand procedure. Pressure signaling inputs to control 24 are provided by discardable flexible tubing 26 extending thereto from exhaust valve 16 within device 14. A supply of life support gas such as oxygen under pressure is represented at block 28 in communication with control 24 through a conduit 30. This supporting gas may be provided through typical gas retaining cylinders, however, it conventionally is supplied for clinical use from supply conduits emanating from a central station. The oxygen-rich supporting gas generally is available to controls as at 24 at a pressure of about 50 p.s.i.g. For purposes of operating the nebulizer device 18, a gas delivery control feature may be provided as represented at block 30. Control 33 communicates with the pressurized supply at block 28 through conduit 32 and supplies gas at this relatively higher pressure through conduit 34 to nebulizer 18. This supply may be provided by control 33 in a pulsing manner over a predetermined duty cycle for the system.

As discussed above, the developement of the optimum mist droplet size distribution according to the invention involves an initial, larger droplet formation followed by a secondary atomization thereof. Accordingly, as a prelude to describing a particular embodiment providing this secondary atomization, an examination of the theory of the breakup mechanism may be found helpful. This breakup mechanism involves the positioning of a liquid droplet of given larger size within a high velocity stream of gas. If the velocity of the droplet, $v_p$, is considerably different than the velocity of the gas surrounding it, $v_g$, a breakup mechanism is observed which is commonly referred to as "secondary atomization". Generally two dominant breakup mechanisms are considered to be associated with this phenomenon which are commonly referred to as a "deformation" mechanism and a "stripping" mechanism. In analyzing these two mechanisms, the following initial flow and droplet variables are considered:

$D_I$ = initial particle (i.e., droplet) diameter
$u_r$ = relative velocity between the particle and the gas stream (i.e., $u_r = v_p - v_g$)
$\rho_g$ = density of gas
$\rho_L$ = density of liquid droplet
$S$ = surface tension of liquid These variables can be associated to develop expressions for determining the presence or absence of secondary atomization. For example, the variables may be associated to derive the Weber number, $W_e$, as a ratio of the ram pressure deformation force that prevails on the windward face of the droplet with respect to the surface tension force (i.e., $S/D_I$) which holds the droplet together. Set forth as an equation, the Weber number is represented by the following expression:

$$W_e = \frac{\rho_g u_r^2}{S/D_I} \quad (1)$$

It may readily be opined that larger Weber number values are required to evoke a fragmentation of droplets. Critical Weber numbers, $W_{ec}$ having values within the range of 10–20 have been reported for fragmentation of liquid droplets, with values thereof from 12–15 being common for droplet fragmentation of distilled water. In this regard, it may be observed that the flow condition set forth below as expression (2) impliedly obtains in the development of secondary atomization.

$$\rho_g u_r^2 \geq W_{ec(S/d)} \quad (2)$$

Also considered in the analysis of secondary atomization is the characteristic droplet oscillation period, $\tau$. This characteristic period is represented by the following expression:

$$\tau = \frac{\pi}{4}\sqrt{\frac{\rho_L D_I^3}{S}} \quad (3)$$

In determining the probable mechanism of secondary fragmentation of the droplet, additionally, it is useful to consider a time variable, $t_a$, in relation to $\tau$, the characteristic droplet oscillation period. This variable, $t_a$, is referred to as the "action time" and, in general terms, is the interval during which an initial droplet or liquid particle is subjected to gas forces reacting upon it under given ram pressure force. The use of the "action time" provides a means for considering the droplet dynamics in determining the droplet breakup mechanism, and has been termed a time constant on the driving force for droplet breakup. Further discussion of the term is described in: Morrell, G., "Critical Conditions for Drop and Jet Shattering", NASA-TN-D677 (1961).

Looking to FIG. 2, breakup phenomena for the case of deformation and stripping mechanism are pictorially revealed. In the figure, a droplet 40 having diameter, $D_I$, is subjected to a relative gas velocity, $u_r$, and consequent ram pressure force represented by the small arrows adjacent the droplet, defined as $\rho_g u_r^2$. As labeled in FIG. 2, with a deformation mechanism, the effect of the ram pressure is to increasingly flatten the drop with time, as shown at step 42. For conditions where $t_a$ is greater than or equal to $\tau$ (i.e. action time exceeds oscillatory period), a critical time is reached where a hole is blown in the droplet to form a structure which resembles a bag with a relatively massive torodial rim and a thin wall, as represented at step 44. Ultimately, the bag-shaped structure bursts producing a shower of much smaller droplets and the rim, containing a major portion of the initial mass of the droplet, grows in diameter until it divides into a number of smaller droplets, as represented at step 46.

For the case of a stripping mechanism, the inertial characteristics of the droplet cause it to maintain a shape that resembles a planetary ellipsoid, as represented at step 48. Subsequently, as represented at step 50, liquid is drawn off in thin sheets from the edge of the droplet and fine ligaments, the thicknesses of which are of the order of the gas-liquid boundary layer thicknesses at the thin sheet attachment points, rapidly disintegrate into very small droplets, hence the term "stripping". Should the initial Weber number not be sufficiently high or if the time interval spent at conditions representing a Weber number above critical value not be sufficiently long, the stripping process will cease and a stable droplet of smaller size will remain in addition to micro mist. This condition is represented at step 52 in FIG. 2.

From the foregoing it may be observed that in order to obtain a complete stripping action, Weber numbers should be large and the characteristic droplet oscillation period, $\tau$, should be small. However, the latter coefficient should have a value sufficient to maintain a continuous stripping activity with time. The action time should be sufficiently long to provide for enough of an interval of reaction to completely strip the droplet and evolve a desired droplet or liquid particle size distribution. Further, the Weber should be kept high so as to maintain a high driving force for this stripping mechanism to persist. It has been the observation of the applicants that the stripping mechanism for secondary droplet breakup will produce a greater number of smaller diameter droplets. Hence, high Weber numbers should be produced for time periods of the order of the characteristic droplet oscillation period in order to provide efficient secondary atomization. Further, it may be implied that there is no theoretical limit for preatomized droplet sizes, i.e. droplet diameters $D_I$, for the free-jet expansion atomization technique as opposed to the utilization of a standing shock wave within a nozzle to carry out droplet breakup.

Looking to FIG. 3, the above consideration defining the parameters for control over a free-jet expansion system are schematically revealed. The drawing shows an initial atomization stage from which region larger droplets having an initial diameter, $D_I$, are introduced along conduit 61 through an access 62 to a droplet containment zone or chamber 64 defined by wall 66. When introduced as entrained within a pressurized gas, the gas and entrained droplets will exhibit a stagnation pressure $P_o$ as well as the noted initial droplet diametric size $D_I$. From chamber 64, the droplets and entraining gas are rapidly expanded through a free-jet, "knife-edge" orifice 70 formed within wall 66. This rapid expansion produces supersonic gas velocities very quickly. However, the droplets cannot be accelerated as rapidly as the gas and a large gas/particle relative velocity is produced in the barrel shock region outlined at 72. Accordingly, the above-discussed considerations for evolving a stripping mechanism mist development are concerned with the reactions carried out within the zone of supersonic flow outlined at 72. For example, the action time within the zone should be gauged with respect to the characteristic droplet oscillation period to achieve the full stripping action as required. Without appropriate control over the developmental parameters of the system, excessively large droplet particles may remain from the stripping action in addition to the desired mist or aerosol represented at 74. The liquid components exiting from the supersonic flow region defined by barrel shock boundary 72 may be considered to represent secondary particles, being the product of the stripping mechanism as shown at 74 as well as a hypothetical remaining original or initial particle having been subjected to stripping to reach a final diameter, $D_F$. The latter particles may be evaluated by known analytical techniques with respect to initial diameter to provide a qualitative efficiency evaluation of the system. It has been determined that optimized liquid particulate size distributions can be achieved through a control over the initial atomization at 60 as well as at the parameters established at the secondary atomization stage commenced within chamber 64.

Figure 4:
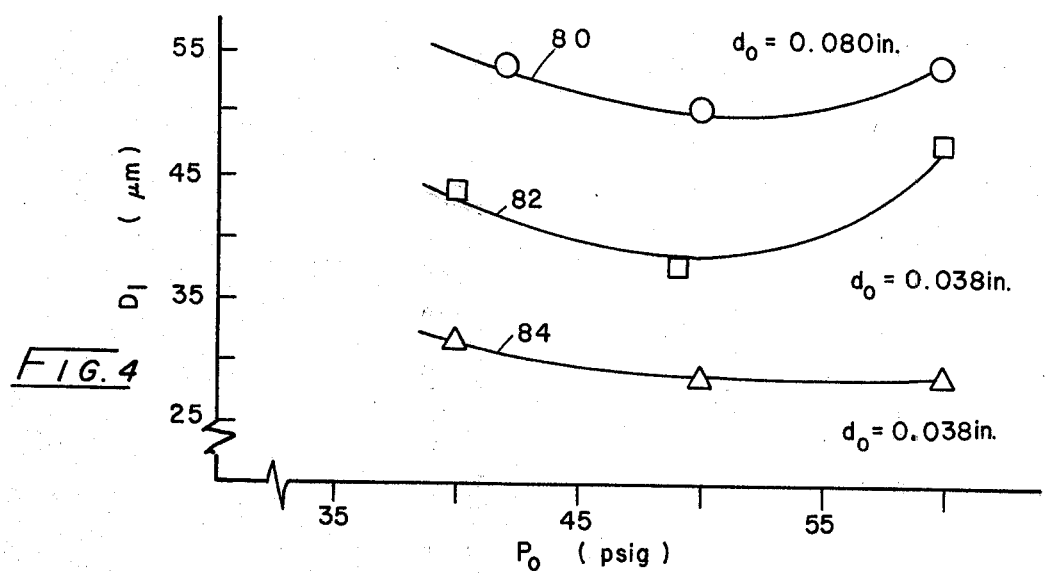
FIG. 4 illustrates a series of curves for various atomizer devices showing the development of initial droplet diameter sizes with respect to stagnation pressure.

Looking to FIG. 4, one aspect of parameter control is revealed through a comparison of curves generated with a free-jet expansion system utilizing two different commercially obtained devices for initial atomization, as described at block 60 in FIG. 3, as well as with a variation of orifice diameters, $d_o$, described at 70 in that figure. These curves, identified at 80, 82 and 84, represent a relative narrow portion of possible plots, falling within a stagnation pressure, $P_o$, range of from about 30 to 60 psig. The curves reveal that initial droplet size, $D_I$, is a function of stagnation pressure, $P_o$, orifice size, $d_o$, and the type of atomizer utilized within the initial atomization stage. Of the curves in FIG. 4, curves 80 and 82 were derived using a "Soni-mist" atomizer, model no. 900-3, a product of Heat Systems Ultrasonic, Inc., Plainview, N.Y., curve 80 being generated with an orifice diameter, $d_o$, of 0.08 inch, and curve 82 is generated with an orifice diameter $d_o$ of 0.038 inch. Curve 84 was generated utilizing a "2-Fluid" device, model no. 15, marketed by the DeVilbiss, Corp. for initial atomization and in conjunction with an orifice size, $d_o$, of 0.038 inch. While initial droplet size appears insensitive to stagnation pressures, $P_o$, within the noted range, excursions beyond that range may well evoke more pronounced variation. It may be observed, that the initial droplet size $D_I$, is somewhat dependent upon orifice size, $d_o$, and particularly, upon the type of commercial first stage atomizer utilized. Accordingly, the curves would appear to indicate that the forms of conventional atomizers presently on the market tend to lack a controlled consistency of droplet development. In deriving the curves of FIG. 4, distilled water was utilized in conjunction with a confined chamber into which the liquid particles of the initial atomization procedure were inserted as entrained within air. All developed droplets, whether in the initial or secondary stage of atomization, were isolated from room air to prevent the possibility of dust entry within the region of measurement for the test system. A Royco particle size analyzer was employed in the study along with a laser fringe visibility analysis for examination of the secondary droplet size $D_S$. Laser fringe visibility techniques were used to measure the initial atomization stage droplet sizes as well as final drop size ($D_f$) after atomization. The Royco particle analyzer was a model 220 which is produced by Royco Instruments, Inc., Menlo Park, California.

The efficiency, $\epsilon$, of the breakup mechanism of the inventive system may be determined by comparing the volume of the droplets of the initial atomization stage 60 which have been converted to desired small secondary droplets of diameter $D_S$, to the volume of particles of initial diameter, $D_I$. The former of these values may be represented as the difference of the cube of the diameter of the particles of initial atomization, $D_I$, minus the cubed value of the diameter, $D_F$, of those particles following the removal of material therefrom in consequence of the above-described stripping mechanism. This conversion efficiency may be expressed as follows:

$$\epsilon = \frac{D_I^3 - D_F^3}{D_I^3} \tag{4}$$

Figure 5:
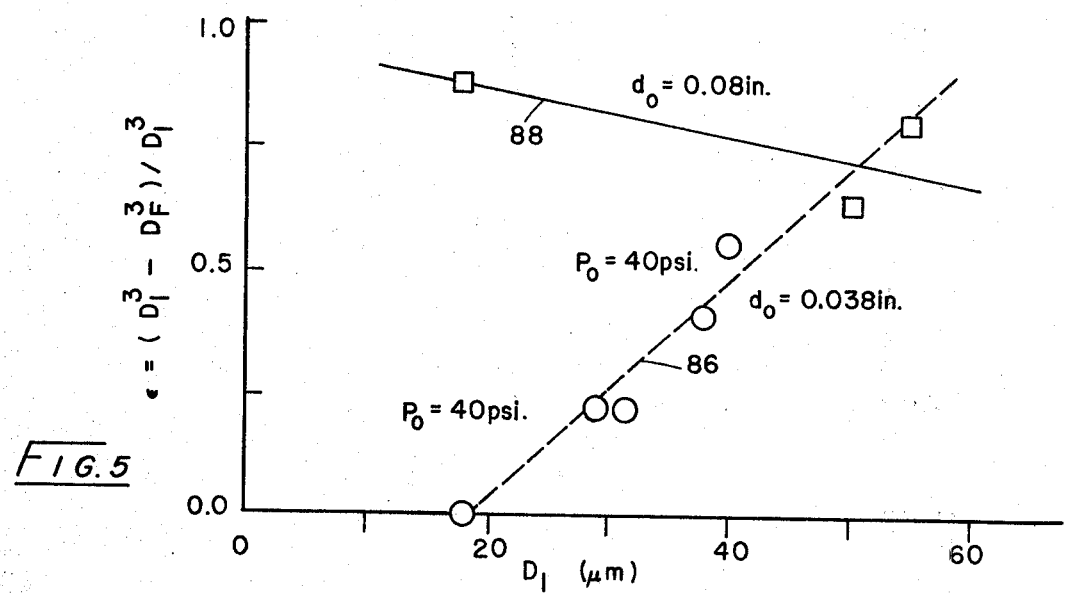
FIG. 5 shows a curve comparison of droplet conversion efficiency with respect to initial stage droplet diameter for two different free-jet orifice diametric sizes.

Looking now to FIG. 5, values of conversion efficiency, $\epsilon$, are plotted with respect to initial atomization stage droplet diameter, $D_I$. As represented by curve 86, while efficiencies were very low for orifice diameters, $d_o$ of 0.038 inch, by increasing the diameter of the droplets generated in the initial atomization stage, the conversion efficiency, $\epsilon$, increases linearly to the order of a fifty percent efficiency conversion value for initial droplets having diameters of 40 microns. It may be further noted from curve 88 that the conversion efficiency, $\epsilon$, for a larger orifice diameter, $d_o$, of 0.08 inch is relatively high but drops slightly as initial particle diameter size, $D_I$, is elevated. In the latter regard, however, the conversion efficiency remains above about fifty percent through initial diameters of about 55 microns. The orifice diameter, $d_o$, utilized in generating curve 88 was 0.08 inch, and stagnation pressure, $P_o$, was 50 psig except where labeled otherwise. The figure additionally serves to show the advantageous predictability and availability of selecting engineering parameters for any given clinical requirement. For example, where the volume of induced lift supportive gases for purposes of nebulization should be maintained at relatively low levels, an orifice diameter, $d_o$, of lesser extent would be selected with some diminishment in conversion efficiency.

Figure 6:
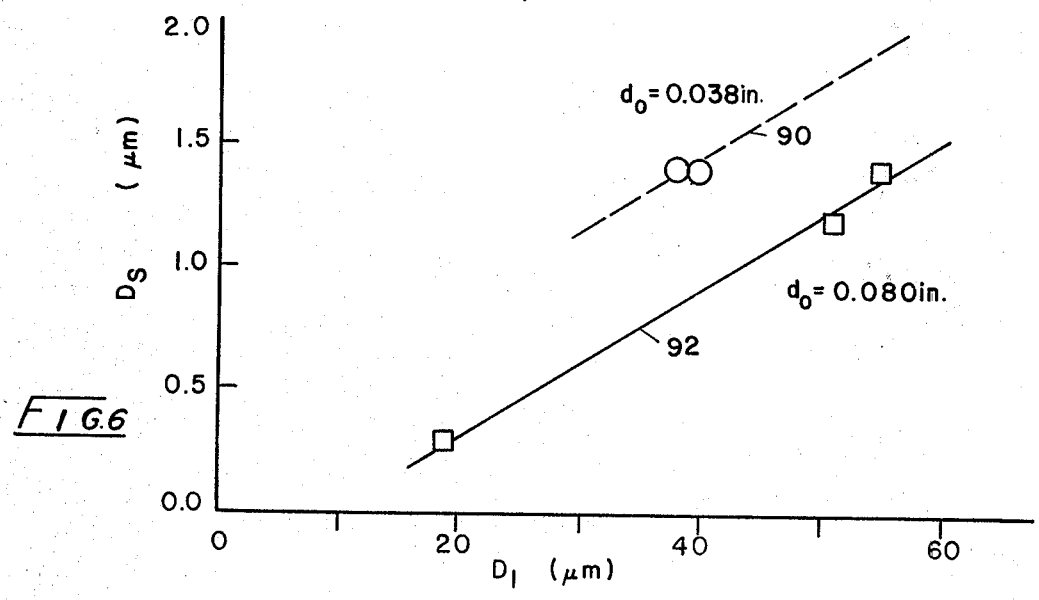
FIG. 6 illustrates curves relating secondary drop size diameter with initial drop size diameter for two values of free-jet orifice diameter.
Figure 7:
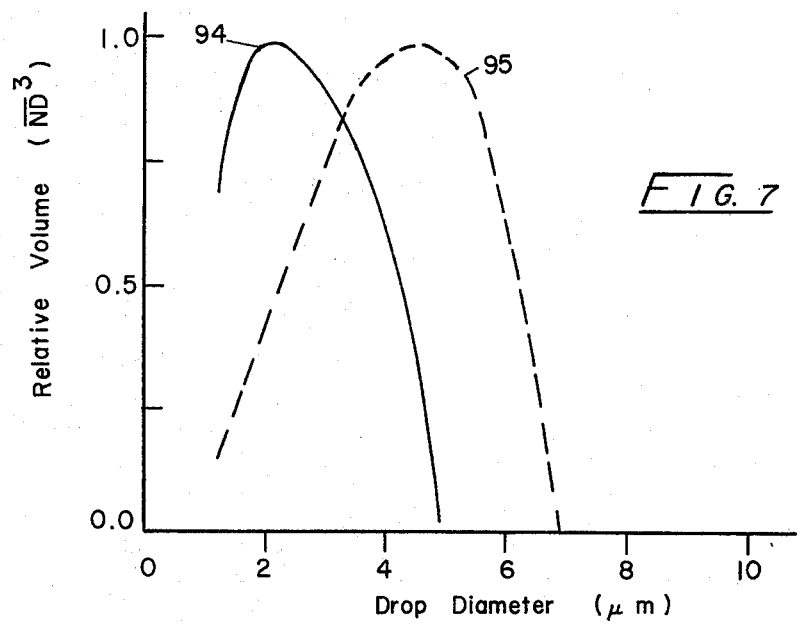
FIG. 7 illustrates two curves relating relative volume of drop distribution with drop diameter.
Figure 8:
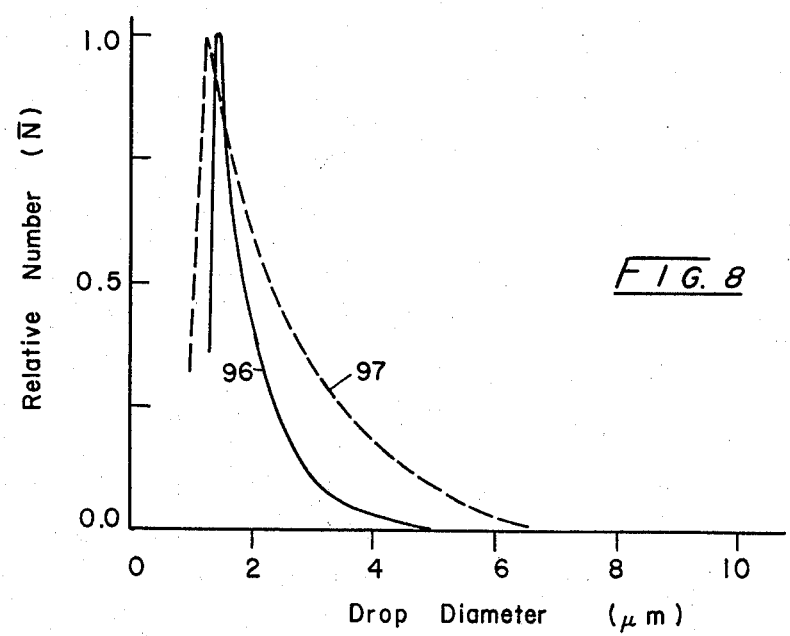
FIG. 8 illustrates two curves relating the number distribution of liquid drop particles with their corresponding diameters.

Looking to FIG. 6, the secondary drop size, represented as the secondary drop diameter, $D_S$, is plotted as a function of initial diameter size, $D_I$. Note from curve 90 derived utilizing an orifice diameter, $d_o$ of 0.038 inch, as well as curve 92 representig an orifice diameter, $d_o$ of 0.08 inch, that the secondary drop diameter increases linearly with initial droplet diameter. This relationship reveals that the size of the particles evolved through the secondary atomization step can be produced within any diametric region desired by the operator. The observation also tends to confirm that the stripping mechanism is most probably operative with the system, inasmuch as the boundary layer of thickness of a drop which, as noted above, serves an important roll in the stripping process, is also related to drop size. The curves of FIGS. 5 and 6 further reveal that excellent conversion efficiencies are possible for drop ranges which are currently of interest in the field of aerosol therapy, i.e. in the range of 1-2 microns diameter.

Considered as a whole, the above discourse indicates that a free-jet atomizer scheme provides a highly advantageous arrangement for generating an adequate number of droplets of proper size for lung therapy applications. This observation is amplified where the respirable drop volume distribution and drop number distribution of the system are examined as a function of secondary diameter. Curve 94 of FIG. 7 was developed utilizing the free jet atomization arrangement of the instant invention, while curve 95 thereof was generated using the above-described conventionally available "Bernoulli" atomizer device currently in clinical use. For each of the curves 94 and 96, the droplet volume is given by the following conventional expression:

$$V_i = \frac{\pi}{6} N_i D_i^3 \quad (5)$$

where $N_i$ is the number of drops with diameter $D_i$ and $V_i$ is the total droplet volume. Curve 94 reveals that the greater portion of liquid droplet volume, and consequently medicament volume, is provided in droplets of preferred 2 micron diameter for the free-jet atomizer technique of the invention. By comparison, the conventional device, represented at curve 95, reveals that the corresponding greater portion of droplet volume is present in droplets of larger diameter, i.e. about 4.5 microns. It is generally considered that droplets having a diameter of about 1–2 microns are more likely to be deposited in the alveoli of the lungs than droplets of greater than 3 micron diameter. Under the latter criterion, the free-jet atomizer system of the invention is indicated as being about twice as effective as the atomizer systems currently in clinical practice.

Looking to FIG. 8 curve 96 is a plot of the respirable drop number distribution with respect to drop diameter for the free-jet atomization arrangement of the invention, while curve 97 represents the corresponding drop number distribution for the above-described conventional "Bernoulli" device. It may be observed that the number distribution represented by curve 96 falls off quite rapidly with increasing drop size, as compared to curve 97. In effect, the results represented by curve 96 tend toward a monodispersed distribution of liquid droplets at the diametric range of interest.

Now looking to FIG. 9, the device 14 incorporating the system of the invention is revealed in more enlarged detail. As described earlier, device 14 includes a mouthpiece 12, exhaust valve assembly and associated tubing 26, and stem support 20 all communicating with and attached to a relatively short rigid tube 21. The end of tube 21 opposite mouthpiece 12 is coupled with a disposable flexible tube 22, in turn, leading to a controlled supply of life supporting gas at relatively low positive pressure, for instance about one-half p.s.i. The nebulizer 18 of the invention includes a cylindrical housing 100 within which is integrally formed an initial atomization chamber 102 and an adjacent, serially disposed containment chamber 104 for receiving entrained liquid droplets of initial diameter, $D_I$. Separating chambers 102 and 104 is a conical, converging duct formed by an inwardly extending annular component 106 having a concave surface 108 the uppermost edge of which defines a relatively wide input aperture 110 leading to chamber 104. The lower surface of chamber 102 is defined by a disc 112 which is configured having a vertically oriented integrally formed nozzle at 114 extending from the center thereof. Disc 112 additionally is configured having one or a plurality of annular passages 116 formed therethrough and communicating in gas transfer relationship with a cup-like reservoir 118. Nozzle 114 is formed having a centrally disposed opening 120 extending therethrough and communicating with a flexible liquid supply tube 122 one end of which is inserted within a corresponding opening formed within disc 112 and the opposite end of which extends to the lowermost region of reservoir 118 to communicate with a medicament conveying liquid represented at 124. Connection between disc 112 and housing 100 is by a threaded engagement shown at 126, while the connection of reservoir 118 therewith is represented by threaded coupling 128. Supporting gas such as oxygen under a higher pressure, for instance 50 p.s.i.g., is introduced through conduit 34 to reservoir 118 by connection thereof with outwardly extending rigid tube 130. Tube 130 is shown as integrally formed with the walls of housing 100.

With the arrangement shown, liquid is drawn (Bernoulli effect) through conduit 122 and thence into nozzle 120 by gas supplied through conduit 34, tube 130, and passages 116. As this liquid exits from nozzle 120, it is broken down into the initial droplet size upon encountering and being entrained by gas passing through passages 116 and into chamber 102. The size of these droplets may be controlled by adjusting the position of the tip of nozzle 120 with respect to the converging duct formed by surface 108. The initial, entrained droplets then are introduced to chamber 104 at the stagnation pressure of the system, whereupon they exit from a knife-edge orifice 132 formed within tube 21. Secondary atomization takes place at this point and the secondary liquid particles are entrained by life supporting gas inserted from tube 22. The gas entrained liquid particles then are delivered along tube 21 to be administered to the patient through mouthpiece 12.

All of the components of the device at FIG. 9 may be configured of suitable polymeric material for fabrication at cost commensurate with the theme of providing disposability of the device following one clinical utilization. In the same light, the threaded connections described may be dispensed with upon the establishing of a desired optimum particulate distribution for a conventional clinical application. In this regard, the stagnation pressure, hole size within nozzle 120 and the relative positioning of the nozzle with respect to conical surface 108 may be pre-established as well as the size of opening 110. As indicated in detail above, the diameter of orifice 132 also contributes to the termination of ultimate particulate distribution.

Since certain changes may be made in the above system, apparatus and method without departing from the scope of the invention herein involved, it is intended that all matter contained in the above description or shown in the accompanying drawings shall be interpreted as illustrative and not in a limiting sense.

What is claimed is:

1. Nebulizer apparatus, connectable with a source of gas and with a liquid source comprising:

a first atomizer stage chamber for simultaneously communicating with a source of pressurized gas and with said source of liquid for forming by the Bernoulli effect a first particulate dispersion of said liquid entrained with said gas, the liquid particles of said first particulate dispersion exhibiting an average diameter, $D_1$, and a surface tension, S, and said gas exhibiting a density $\rho g$;

a containment chamber embodying a second atomizer stage communicating through an input aperture narrower than the chamber with said first atomizer stage and having an input zone for receiving said first particulate dispersion at a stagnation pressure, $P_o$, and including a knife-edge exit orifice having diameter, $d_o$, to effect the expulsion through said exit orifice of said first particulate dispersion to impart supersonic velocities to said gas under flow conditions according to the expression:

$$o_g u_r^2 \geq W_e S / D_I, \text{ where}$$

$u_r$ is the relative velocity between a given said liquid particle and the velocity of said gas, and $W_e$ is Weber number of value effective to effect a breakdown of said liquid particles to form a second gas entrained particulate dispersion of said liquid having an average particle diameter, $D_S$, less than said diameter, $D_I$; and a flexible tube communicating at one end with a source of gas under relatively low positive pressure, at the other end with a mouthpiece, and between the ends with said exit orifice whereby the second gas entrained particulate dispersion and low positive pressure gas are delivered to the mouthpiece.

2. The apparatus of claim 1 in which said Weber number, $W_e$, has a value with respect to a critical value thereof, $W_{ec}$, selected to effect said particle breakdown by a stripping mechanism, in accordance with the expression:

$$W_e/W_{ec} \geq 1.$$

3. The apparatus of claim 1 in which:

said liquid particles of said first dispersion exhibit a characteristic particle oscillation period, $\tau$; and said second atomizer stage is configured for developing a barrel shock region adjacent said exit orifice having an extent sufficient to effect a supersonic velocity gas breakdown influence over said particles for an action time interval, $t_a$, equal to or greater than said oscillation period, $\tau$.

4. The apparatus of claim 1 in which the value of said exit orifice diameter, $d_o$, is selected to derive a liquid particle conversion efficiency, $\epsilon$, of at least about fifty percent.

5. The apparatus of claim 4 in which said stagnation pressure, $P_o$, is about 50 p.s.i.g.

6. The apparatus of claim 1 including means for effecting the passage of said pressurized gas into said first chamber to establish a flow therethrough in a predetermined direction; means defining a nozzle having an outlet communicating in liquid flow relationship with said liquid source and oriented within said first chamber to deliver said liquid within said pressurized gas flow to effect the said formation and entrainment of droplet particles exhibiting said average particle diameter, $D_I$.

7. The apparatus of claim 6 wherein said first chamber outlet means comprises a conical duct converging to an orifice, said orifice being positioned for effecting the passage of said first particulate dispersion into said second atomizer stage means input zone.

8. The apparatus of claim 1 wherein said containment chamber is configured to define said input zone, said exit orifice being situated remotely from said input aperture.

9. The apparatus of claim 1 in which said first chamber and said containment chamber are formed in mutual adjacency within a sanitary housing.

10. The apparatus of claim 9 in which said means defining said nozzle is threadably connected with said housing so as to permit the adjustable positioning thereof with respect to said outlet means.

* * * * *